US009089683B2

(12) United States Patent
Mishelevich (10) Patent No.: US 9,089,683 B2
(45) Date of Patent: *Jul. 28, 2015

(54) NEUROMODULATION METHOD VIA DEEP-BRAIN STIMULATION

(71) Applicant: David J. Mishelevich, Playa del Rey, CA (US)

(72) Inventor: David J. Mishelevich, Playa del Rey, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/609,427

(22) Filed: Jan. 29, 2015

(65) Prior Publication Data

US 2015/0165239 A1 Jun. 18, 2015

Related U.S. Application Data

(63) Continuation of application No. 13/035,962, filed on Feb. 26, 2011, now Pat. No. 8,956,277.

(60) Provisional application No. 61/308,987, filed on Feb. 28, 2010.

(51) Int. Cl.
| | |
|---|---|
| *A61F 5/00* | (2006.01) |
| *A61N 7/00* | (2006.01) |
| *A61N 5/00* | (2006.01) |
| *A61N 5/06* | (2006.01) |
| *A61B 18/02* | (2006.01) |
| *A61N 1/36* | (2006.01) |
| *A61N 5/10* | (2006.01) |
| *A61N 2/00* | (2006.01) |
| *A61H 19/00* | (2006.01) |
| *A61N 1/05* | (2006.01) |
| *A61B 18/00* | (2006.01) |

(52) U.S. Cl.
CPC . *A61N 7/00* (2013.01); *A61B 18/02* (2013.01); *A61H 19/30* (2013.01); *A61H 19/40* (2013.01); *A61N 1/36014* (2013.01); *A61N 1/36107* (2013.01); *A61N 2/006* (2013.01); *A61N 5/00* (2013.01); *A61N 5/0622* (2013.01); *A61N 5/10* (2013.01); *A61B 2018/00982* (2013.01); *A61H 2201/10* (2013.01); *A61H 2205/087* (2013.01); *A61N 1/0534* (2013.01)

(58) Field of Classification Search
CPC ... A61N 7/00; A61N 2/02; A61N 2007/0026; A61N 2007/0078; A61F 5/41
USPC ................ 600/38–41; 128/897–898; 601/1–3
See application file for complete search history.

(56) References Cited

U.S. PATENT DOCUMENTS 8,086,296 B2 * 12/2011 Bystritsky ..................... 600/411
8,956,277 B2 * 2/2015 Mishelevich .................. 600/38

* cited by examiner

Primary Examiner — Samuel Gilbert (57) ABSTRACT

It is the purpose of this invention to provide methods and systems for non-invasive deep brain neuromodulation using ultrasound for the treatment of anorgasmia, hypo-orgasmia, and for the production of orgasms (Orgasmatron). This can include impacting one or multiple points in a neural circuit to produce Long-Term Potentiation (LTP) or Long-Term Depression (LTD). The ultrasound transducers are attached at fixed positions on a holder. Use of ancillary monitoring or imaging to provide feedback is optional. Control of the ultrasonic transducers includes control of direction of the energy emission, intensity, frequency, and phase/intensity relationships to targeting and accomplishing up-regulation and/or down-regulation.

20 Claims, 8 Drawing Sheets

| TARGET | REGULATION |
|---|---|
| DACG | Up |
| Left Lateral OFC | Down |
| Insula | Up |
| Amygdala | Down |
| Cerebellum | Up |
| Temporal Lobe | Down |
| Hippocampus | Down |
| Paraventricular Nucleus of Hypothalamus | Up |
| Nucleus Accumbens | Up |
| Ventral Tegmental Area (VTA) | Up |
| Periductal Grey (PAG) | Up |

NEUROMODULATION METHOD VIA DEEP-BRAIN STIMULATION

CROSS REFERENCE TO RELATED APPLICATIONS

This patent application is a continuation of Non-Provisional patent application Ser. No. 13/035,962, filed Feb. 26, 2011, entitled "ORGASMATRON VIA DEEP-BRAIN NEUROMODULATION," that claims priority to Provisional Patent Application No. 61/308,987, filed Feb. 28, 2010, entitled "ORGASMATRON VIA DEEP-BRAIN NEUROMODULATION." The disclosures of these patent applications are herein incorporated by reference in their entirety.

INCORPORATION BY REFERENCE

All publications, including patents and patent applications, mentioned in this specification are herein incorporated by reference in their entirety to the same extent as if each individual publication was specifically and individually cited to be incorporated by reference.

FIELD OF THE INVENTION

Described herein are systems and methods for Ultrasound Neuromodulation related to orgasm.

BACKGROUND OF THE INVENTION

It has been demonstrated that focused ultrasound directed at neural structures can stimulate those structures. If neural activity is increased or excited, the neural structure is said to be up regulated; if neural activated is decreased or inhibited, the neural structure is said to be down regulated. Neural structures are usually assembled in circuits. For example, nuclei and tracts connecting them make up a circuit. The potential application of ultrasonic therapy of deep-brain structures has been suggested previously (Gavrilov L R, Tsirulnikov E M, and I A Davies, "Application of focused ultrasound for the stimulation of neural structures," Ultrasound Med Biol. 1996;22(2):179-92. and S. J. Norton, "Can ultrasound be used to stimulate nerve tissue?," BioMedical Engineering OnLine 2003, 2:6). Norton notes that while Transcranial Magnetic Stimulation (TMS) can be applied within the head with greater intensity, the gradients developed with ultrasound are comparable to those with TMS. It was also noted that monophasic ultrasound pulses are more effective than biphasic ones. Instead of using ultrasonic stimulation alone, Norton applied a strong DC magnetic field as well and describes the mechanism as that given that the tissue to be stimulated is conductive that particle motion induced by an ultrasonic wave will induce an electric current density generated by Lorentz forces.

The effect of ultrasound is at least two fold. First, increasing temperature will increase neural activity. An increase up to 42 degrees C. (say in the range of 39 to 42 degrees C.) locally for short time periods will increase neural activity in a way that one can do so repeatedly and be safe. One needs to make sure that the temperature does not rise about 50 degrees C. or tissue will be destroyed (e.g., 56 degrees C. for one second). This is the objective of another use of therapeutic application of ultrasound, ablation, to permanently destroy tissue (e.g., for the treatment of cancer). An example is the ExAblate device from InSightec in Haifa, Israel. The second mechanism is mechanical perturbation. An explanation for this has been provided by Tyler et al. from Arizona State University (Tyler, W. J., Y. Tufail, M. Finsterwald, M. L. Tauchmann, E. J. Olsen, C. Majestic, "Remote excitation of neuronal circuits using low-intensity, low-frequency ultrasound," PLoS One 3(10): e3511, doi:10.137/1/journal.pone.0003511, 2008)) where voltage gating of sodium channels in neural membranes was demonstrated. Pulsed ultrasound was found to cause mechanical opening of the sodium channels, which resulted in the generation of action potentials. Their stimulation is described as Low Intensity Low Frequency Ultrasound (LILFU). They used bursts of ultrasound at frequencies between 0.44 and 0.67 MHz, lower than the frequencies used in imaging. Their device delivered 23 milliwatts per square centimeter of brain—a fraction of the roughly 180 mW/cm$^2$ upper limit established by the U.S. Food and Drug Administration (FDA) for womb-scanning sonograms; thus such devices should be safe to use on patients. Ultrasound impact to open calcium channels has also been suggested.

Alternative mechanisms for the effects of ultrasound may be discovered as well. In fact, multiple mechanisms may come into play, but, in any case, this would not effect this invention.

Approaches to date of delivering focused ultrasound vary. Bystritsky (U.S. Pat. No. 7,283,861, Oct. 16, 2007) provides for focused ultrasound pulses (FUP) produced by multiple ultrasound transducers (said preferably to number in the range of 300 to 1000) arranged in a cap place over the skull to effect a multi-beam output. These transducers are coordinated by a computer and used in conjunction with an imaging system, preferable an fMRI (functional Magnetic Resonance Imaging), but possibly a PET (Positive Emission Tomography) or V-EEG (Video-Electroencephalography) device. The user interacts with the computer to direct the FUP to the desired point in the brain, sees where the stimulation actually occurred by viewing the imaging result, and thus adjusts the position of the FUP according. The position of focus is obtained by adjusting the phases and amplitudes of the ultrasound transducers (Clement and Hynynen, "A non-invasive method for focusing ultrasound through the human skull," Phys. Med. Biol. 47 (2002) 1219-1236). The imaging also illustrates the functional connectivity of the target and surrounding neural structures. The focus is described as two or more centimeters deep and 0.5 to 1000 mm in diameter or preferably in the range of 2-12 cm deep and 0.5-2 mm in diameter. Either a single FUP or multiple FUPs are described as being able to be applied to either one or multiple live neuronal circuits. It is noted that differences in FUP phase, frequency, and amplitude produce different neural effects. Low frequencies (defined as below 300 Hz.) are inhibitory. High frequencies (defined as being in the range of 500 Hz to 5 MHz) are excitatory and activate neural circuits. This works whether the target is gray or white matter. Repeated sessions result in long-term effects. The cap and transducers to be employed are preferably made of non-ferrous material to reduce image distortion in fMRI imaging. It was noted that if after treatment the reactivity as judged with fMRI of the patient with a given condition becomes more like that of a normal patient, this may be indicative of treatment effectiveness. The FUP is to be applied 1 ms to 1 s before or after the imaging. In addition a CT (Computed Tomography) scan can be run to gauge the bone density and structure of the skull.

An alternative approach is described by Deisseroth and Schneider (U.S. patent application Ser. No. 12/263,026 published as US 2009/0112133 A1, Apr. 30, 2009) in which modification of neural transmission patterns between neural structures and/or regions is described using ultrasound (including use of a curved transducer and a lens) or RF. The impact of Long-Term Potentiation (LTP) and Long-Term Depression (LTD) for durable effects is emphasized. It is noted that ultrasound produces stimulation by both thermal and mechanical impacts. The use of ionizing radiation also appears in the claims.

Adequate penetration of ultrasound through the skull has been demonstrated (Hynynen, K. and F A Jolesz, "Demonstration of potential noninvasive ultrasound brain therapy through an intact skull," Ultrasound Med Biol, 1998 Feb;24 (2):275-83 and Clement G T, Hynynen K (2002) A non-invasive method for focusing ultrasound through the human skull. Phys Med Biol 47: 1219-1236.). Ultrasound can be focused to 0.5 to 2 mm as TMS to 1 cm at best.

Komisaruk, Whipple, and their colleagues have provided significant information about the correlation between orgasm and imaging for both women and men using vaginal-cervical mechanical self-stimulation (CSS) or imagining in intact women and in other areas where there has been spinal cord injury (Komisaruk B. R. and B. Whipple, "Functional MRI of the brain during orgasm in women," Annu Rev Sex Res., 16:62-86, 2005 and Komisaruk, B. R., Whipple, B., Crawford, A., Grimes, S., Liu, W.-C., Kalnin, A, and K. Mosier, "Brain activation during vaginocervical self-stimulation and orgasm in women with complete spinal cord injury: fMRI evidence of mediation by the Vagus nerves," Brain Research 1024 (2004) 77-88, 2004). There is not much difference between the sexual responses of men's and women's brains.

In both women and me, the brain regions that activated (as judged by PET or fMRI scanning) are:
1. Cingulate Gyms (pain circuit)
2. Insula (pain circuit)
3. Amygdala (regulates emotions)
4. Nucleus Accumbens (controls dopamine release)
5. Ventral Tegmental Area (VTA) (actually releases the dopamine)
6. Hippocampus (memory)
7. Cerebellum (controls muscle function)
8. Paraventricular Nucleus of the Hypothalamus and Pituitary Gland (beta-endorphin release (decreases pain), oxytocin release (increases feelings of trust), and vasopressin (increases bonding)

In women there is activation of the Periaqueductal Gray (PAG) (controlling the "flight or fight" response). The Amygdala and Hippocampus (which deal with fear and anxiety) show decreased activity—perhaps because women have more of a need to feel safe and relaxed in order to enjoy sex. In both women and men, the Left Lateral Orbitofrontal Cortex and the Temporal Lobes shut down during orgasm.

Sexually related sensory signals come from the vagina, cervix, clitoris, and uterus in women. In terms of transmission through nerve distribution:
1. Hypogastric Nerve (uterus and the cervix in women; prostate in men)
2. Pelvic Nerve (vagina and cervix in women; rectum in both sexes)
3. Pudendal Nerve (clitoris in women; scrotum and penis in men)
4. Vagus Nerve (cervix, uterus and vagina (true whether or not the spinal cord is intact)

Women can also have orgasms from stimulation of many parts of their bodies are stimulated (e.g., mouth, the nipples, the anus, hand). In women and men with spinal cord injuries, orgasms have been described when skin is stimulated around the level of the injury because of the heightened sensitivity there. Women can have orgasms without touching their body through imagery alone.

A peripheral Orgasmatron is known in that in 2004 Dr. Stuart Meloy, an anesthesiologist and pain expert in Winston-Salem, N.C., reported that sacral nerve stimulation with an implanted electrode resulted in an orgasm in ten of eleven women being treated for other conditions (Meloy, T. S. & Southern, J. P. "Neurally Augmented Sexual Function in Human Females: A Preliminary Investigation," Neuromodulation Volume 9, No. 1 (2006): 34-40).

It would be desirable to apply ultrasound neuromodulation to the treatment of anorgasmia, hypo-orgasmia, and for the production of orgasms (Orgasmatron).

SUMMARY OF THE INVENTION

It is the purpose of this invention to provide methods and systems for non-invasive deep brain neuromodulation using ultrasound for the treatment of anorgasmia, hypo-orgasmia, and for the production of orgasms (Orgasmatron). One source of anorgasmia or hypo-orgasmia in men is the impact of treatment for prostate cancer. This can include impacting one or multiple points in a neural circuit to produce acute effects or Long-Term Potentiation (LTP) or Long-Term Depression (LTD). The ultrasound transducers are attached at fixed positions on a track. Use of ancillary monitoring or imaging to provide feedback is optional. In embodiments were concurrent imaging is to be done, the device of the invention is to be constructed of non-ferrous material. A shell can also optionally cover the apparatus. Control of the ultrasonic transducers includes control of direction of the energy emission, intensity, frequency, and phase/intensity relationships to targeting and accomplishing up regulation and/or down regulation.

The targeting can be done with one or more of known external landmarks, an atlas-based approach (e.g., Tailarach or other atlas used in neurosurgery) or imaging (e.g., fMRI or Positron Emission Tomography). The imaging can be done as a one-time set-up or at each session although not using imaging or using it sparingly is a benefit, both functionally and the cost of administering the therapy.

While ultrasound can be focused down to a diameter on the order of one to a few millimeters (depending on the frequency), whether such a tight focus is required depends on the conformation of the neural target. For example, some targets, like the Cingulate Gyms, are elongated and will be more effectively served with an elongated ultrasound field at the target.

Ultrasound stimulation uses smaller and less expensive devices than other means of deep-brain neuromodulation such as Transcranial Magnetic Stimulation. The current invention is sufficiently portable to be practical for home use.

BRIEF DESCRIPTION OF THE DRAWINGS

FIG. 2A shows an Ultrasound Transducer Basic Array without ultrasound conduction meeting and FIG. 2B with.

DETAILED DESCRIPTION OF THE INVENTION

It is the purpose of this invention to provide methods and systems for non-invasive deep brain neuromodulation using ultrasound for the treatment of anorgasmia, hypo-orgasmia, by the production of orgasms (Orgasmatron) or facilitation of having orgasms. One source of anorgasmia or hypo-orgasmia in men is the impact of treatment for prostate cancer. It would be possible to use the Orgasmatron of this invention for recreational uses, including hedonic stimulation, as well. This can include impacting one or multiple points in a neural circuit to produce acute effects or Long-Term Potentiation (LTP) or Long-Term Depression (LTD). While use of a single target would be unusual, for a given patient, neuromodulation may cause short or long-term orgasmic effects. As to long-term effects, the application of the Orgasmatron invention may result in orgasms or hedonic effects with lower Orgasmatron stimulation, lower other stimulation, or no need for the Orgasmatron at all. The invention works because an orgasm is a event in the brain, not the peripheral nervous system. Neuromodulation of the same deep-brain targets that are involved in orgasm elicited through other means will result in an orgasm.

The stimulation frequency for inhibition is 300 Hz or lower (depending on condition and patient). The stimulation frequency for excitation is in the range of 500 Hz to 5 MHz. In this invention, the ultrasound acoustic frequency is in range of 0.3 MHz to 0.8 MHz to permit effective transmission through the skull with power generally applied less than 60 mW/cm$^2$ but also at higher target- or patient-specific levels at which no tissue damage is caused. The acoustic frequency (e.g., 0.44 MHz that permits the ultrasound to effectively penetrate through skull and into the brain) is gated at the lower rate to impact the neuronal structures as desired (e.g., say 300 Hz for inhibition (down regulation) or 1 kHz for excitation (up regulation). If there is a reciprocal relationship between two neural structures (i.e., if the firing rate of one goes up the firing rate of the other will decrease), it is possible that it would be appropriate to hit the target that is easiest to obtain the desired result. For example, one of the targets may have critical structures close to it so if it is a target that would be down regulated to achieve the desired effect, it may be preferable to up-regulate its reciprocal more-easily-accessed or safer reciprocal target instead. The frequency range allows penetration through the skull balanced with good neural-tissue absorption. Ultrasound therapy can be combined with therapy using medication or other devices (e.g., Transcranial Magnetic Stimulation (TMS), transcranial Direct Current Stimulation (tDCS), Radio-Frequency (RF) therapy, application of optogenetics, cryotherapy, stereotactic radiosurgery, and/or Deep Brain Stimulation (DBS) using implanted electrodes).

The lower bound of the size of the spot at the point of focus will depend on the ultrasonic frequency, the higher the frequency, the smaller the spot. Ultrasound-based neuromodulation operates preferentially at low frequencies relative to say imaging applications so there is less resolution. As an example, let us have a hemispheric transducer with a diameter of 3.8 cm. At a depth approximately 7 cm the size of the focused spot will be approximately 4 mm at 500 kHz where at 1 Mhz, the value would be 2 mm. Thus in the range of 0.4 MHz to 0.7 MHz, for this transducer, the spot sizes will be on the order of 5 mm at the low frequency and 2.8 mm at the high frequency.

Figure 1:
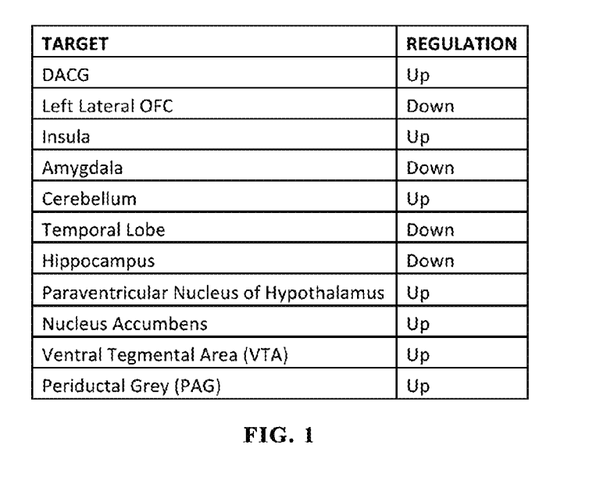
FIG. 1 Table of Targets.

FIG. 1 shows a table of targets relevant to orgasms and whether the target is to be up regulated or down regulated. For example, targets like the Dorsal Anterior Cingulate Gyrus (DACG), Insula, Cerebellum, and Nucleus Accumbens are up regulated and others like the Left Lateral OFC, and the Temporal Lobe are down regulated. Not all the targets listed in the table need to be involved in a given Orgasmatron. How many are needed is patient specific.

Figure 2A:
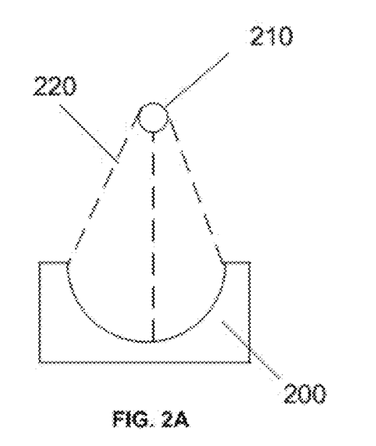
Figure 2B:
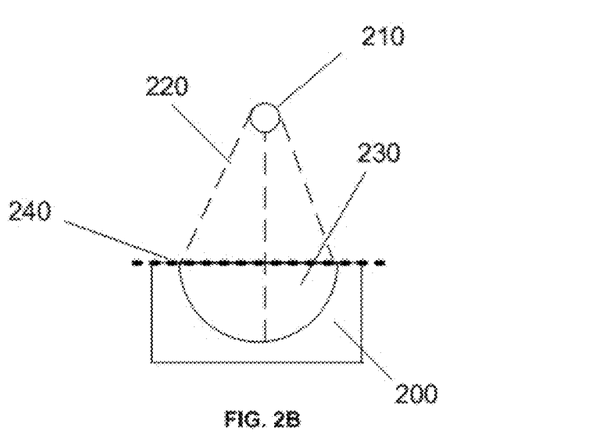

FIG. 2 illustrates the Ultrasound Transducer Basic Array. FIG. 2A shows the configuration without ultrasound conduction medium. Transducer array 200 is aimed towards target 210 with target 210 hit by ultrasound field 220. In FIG. 2B, transducer 200 again is aimed at target 210 with target 210 hit by ultrasound field 220. In this case, ultrasound conduction medium (e.g., silicone oil contained in a pouch or Dermasol from California Medical Innovations) 230 is pressed against the head with the interface provided by ultrasound conduction gel layer 240. The line of ultrasound conduction gel 240 is the outside of the head. Transducer array assemblies of this type may be supplied to custom specifications by Imasonic in France (e.g., large 2D High Intensity Focused Ultrasound (HIFU) hemispheric array transducer)(Fleury G., Berriet, R., Le Baron, O., and B. Huguenin, "New piezocomposite transducers for therapeutic ultrasound," 2$^{nd}$ International Symposium on Therapeutic Ultrasound—Seattle—31/07-02 Aug. 02), typically with numbers of ultrasound transducers of 300 or more. Blatek and Keramos-Etalon in the U.S. are other custom-transducer suppliers. The power applied will determine whether the ultrasound is high intensity or low intensity (or medium intensity) and because the ultrasound transducers are custom, any mechanical or electrical changes can be made, if and as required. At least one configuration available from Imasonic (the HIFU linear phased array transducer) has a center hole for the positioning of an imaging probe. Keramos-Etalon also supplies such configurations. The ultrasound field can be steered control of phase and amplitude producing the direction and focus.

Figure 3:
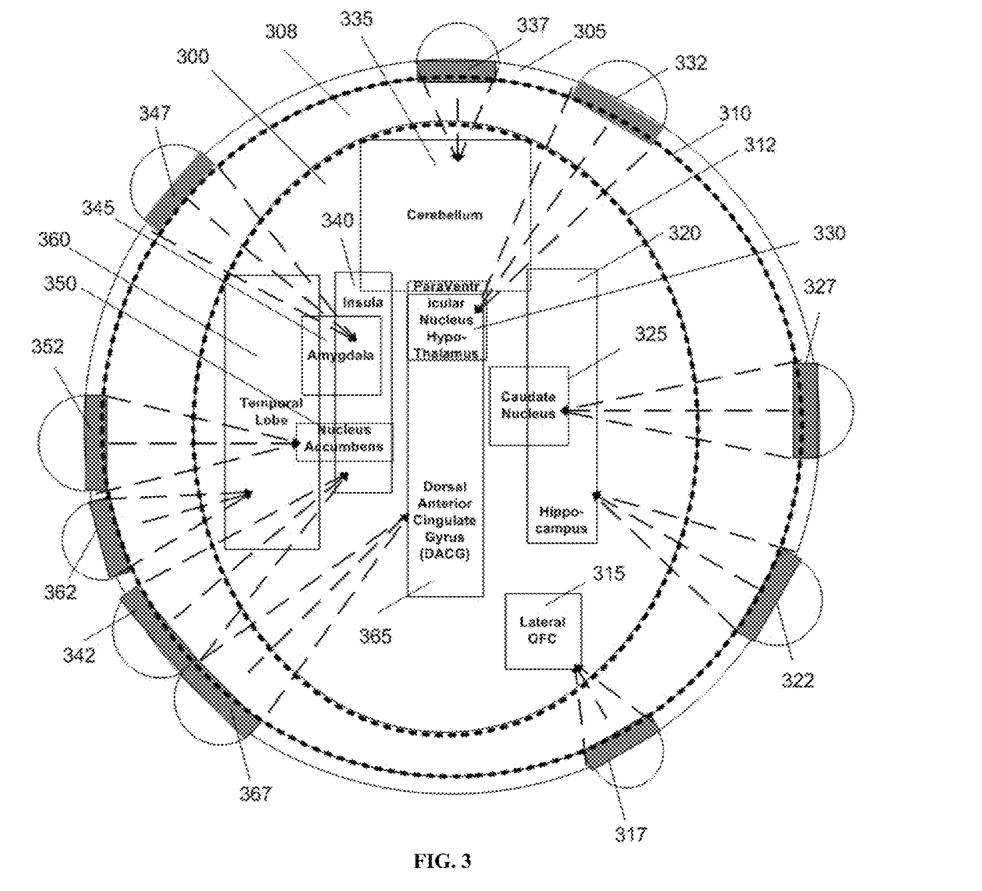
FIG. 3 Ultrasound Transducer Configuration.

FIG. 3 illustrates the ultrasound transducer configuration for the Orgasmatron. Again, not all the targets need be covered in a given Orgasmatron. How many is be patient specific. For the effective ultrasound transmission to and through the skull and to brain targets, coupling must be put into place. Head 300 is surrounded by ultrasound-transducer holder 305 with ultrasound conduction medium 308 in between with ultrasound-conduction gel layers 310 and 312 providing the interfaces between the ultrasound transducers and the ultrasound-conduction medium 308 for the former and ultrasound-conduction medium 308 and the head 300 for the latter. The locations and orientations of the holders can be calculated by locating the applicable targets relative to atlases of brain structure such as the Tailarach atlas and/or imaging as discussed below.

The ultrasound transducers are arranged on the ultrasound-transducer holders 305 with ability (not shown) to move the ultrasound transducers radially in and out to achieve ultrasound focus. Going counterclockwise, target Lateral Orbito-Frontal Cortex (OFC) 315 is targeted by ultrasound transducer 317, target Hippocampus 320 is targeted by ultrasound transducer 322, target Caudate Nucleus 325 is targeted by ultrasound transducer 327, target Paraventricular Nucleus of the Hypothalamus 330 is targeted by ultrasound transducer 332, target Cerebellum 335 is targeted by ultrasound transducer 337, target Amygdala 345 is targeted by ultrasound transducer 347, target Nucleus Accumbens 350 is targeted by ultrasound transducer 352, target Temporal Lobe 360 is targeted by ultrasound transducer 362, target Insula 340 is targeted by ultrasound transducer 342, and target Dorsal Anterior Cingulate Gyrus (DACG) 365 is targeted by ultrasound transducer 367. The vertical positions in some configurations will be obtained by displacing ultrasound transducers above or below holder 305. In other embodiments, vertical positioning will be obtained by beam steering the ultrasound fields by varying the phase and intensity relationships.

Figure 4:
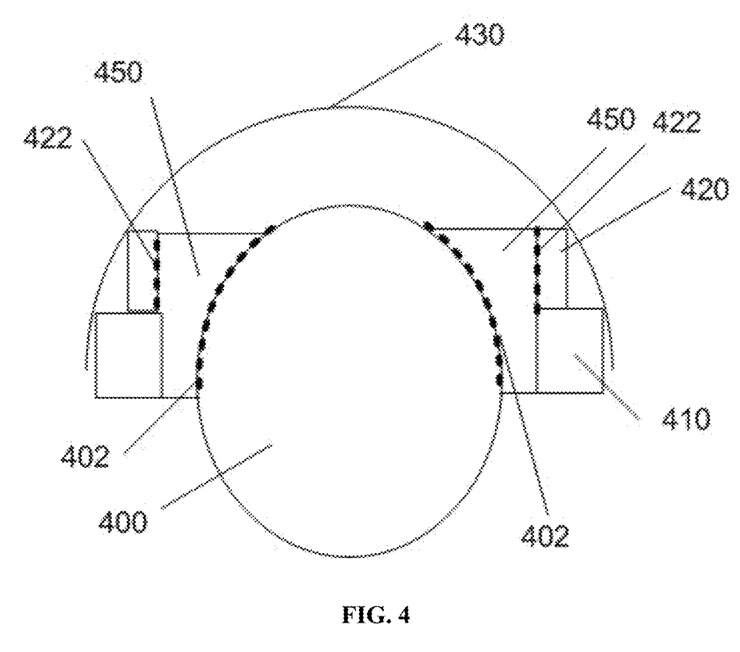
FIG. 4 Ultrasound Transducer Configuration covered by a shell.

FIG. 4 shows the ultrasound transducer configuration covered by a shell. Head 400 is surrounded by ultrasound-transducer holder 410 with its ultrasound transducers 420 with ultrasound-conduction medium 450 filling the space between ultrasound transducers 420 and head 400 with the ultrasound conduction gel layers 422 and 402 respectively providing the interfaces between ultrasound transducer 422 and ultrasound-conduction medium 450 and ultrasound-conduction medium 450 and head 400. The apparatus is covered by protective shell 430. In one embodiment, a Computer-Aided Manufacturing (CAM) process creates the positions in the holder 410 with input from atlas coordinates and/or patient specific imaging (e.g., fMRI or PET). Once the individual set-up of ultrasonic transducer has been determined as covered below, then a personal portable model for a given patient/subject can be built with computer-aided manufactured holder or holders in a potentially flexible holder assembly can be fixed in place.

Figure 5:
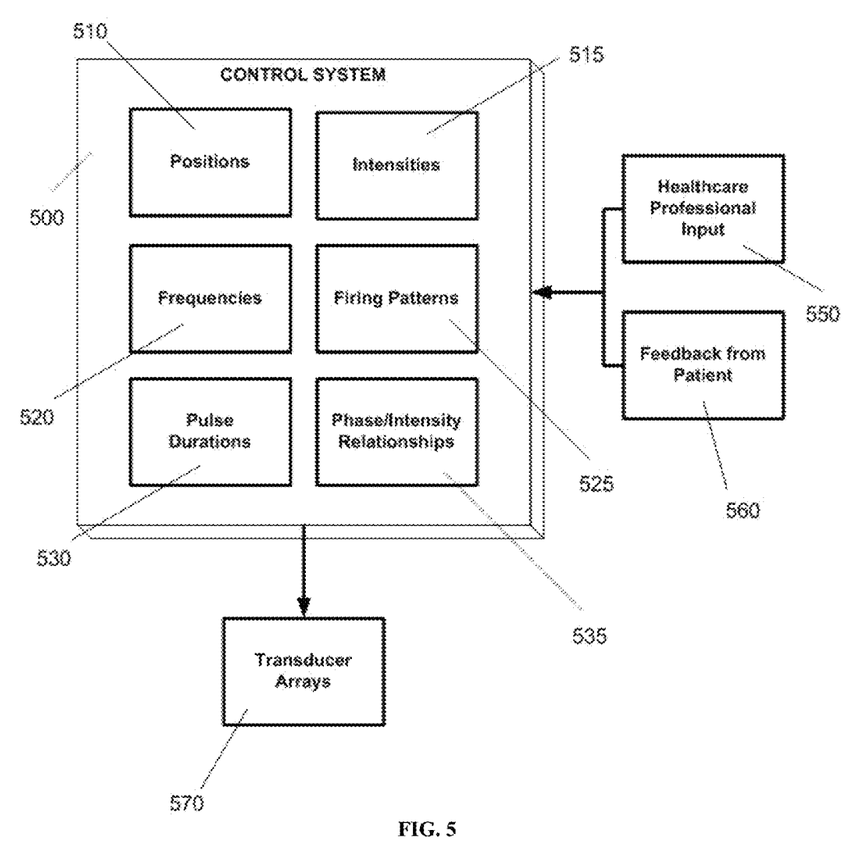
FIG. 5 Control Circuit.

FIG. 5 shows the Control Circuit 500 with its controlled variables (variable for each individual ultrasound transducer array in the set of transducer arrays 570) positions 510, intensities 515, frequencies 520, firing patterns 525, pulse durations 530, and phase/intensity relationships 535. These variables are all plural because of a set of ultrasound transducer arrays are controlled. Input comes from healthcare profession input 550 and feedback from patient 560. Feedback from patient 560 provides for a mechanism for the patient to tune the system to optimize personal effect.

Figure 6:
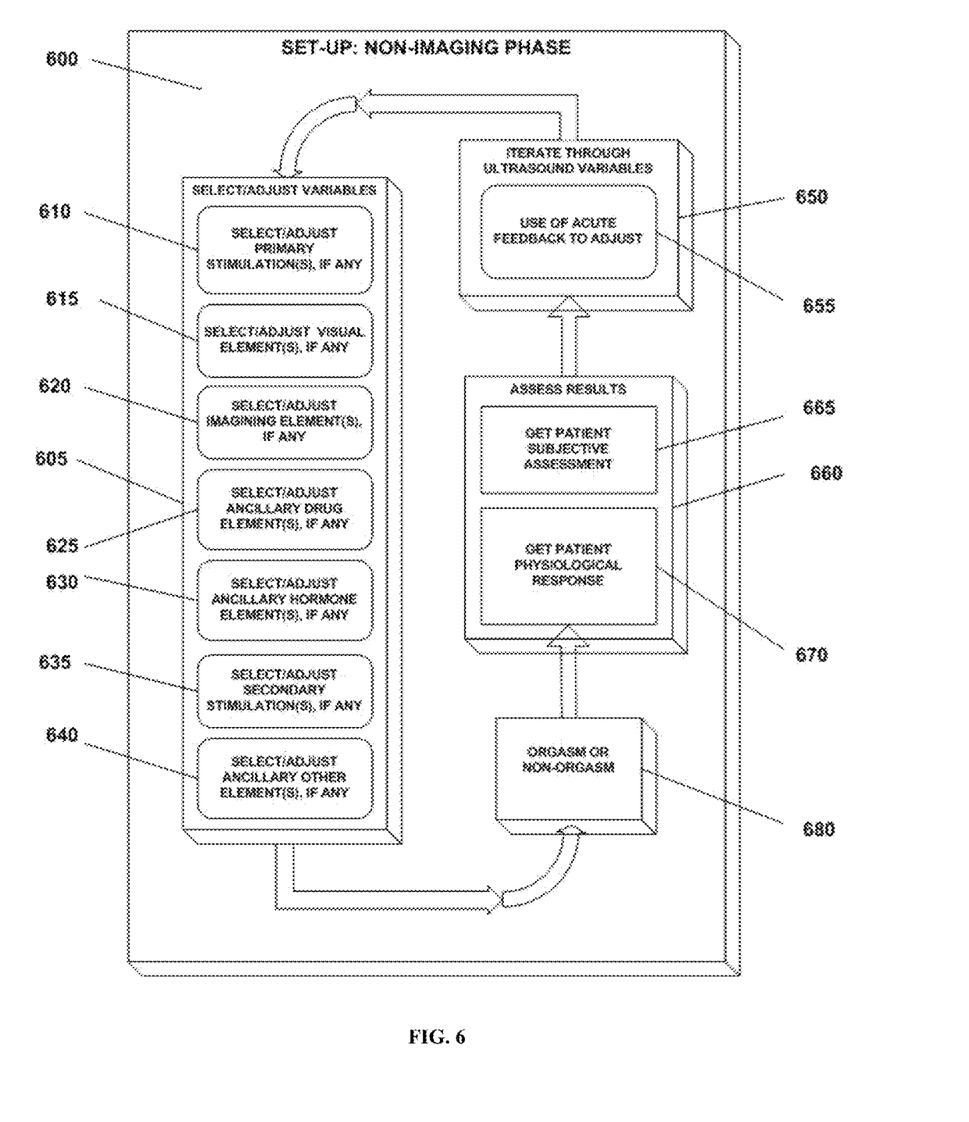
FIG. 6 Set-Up Non-Imaging Phase.
Figure 7:
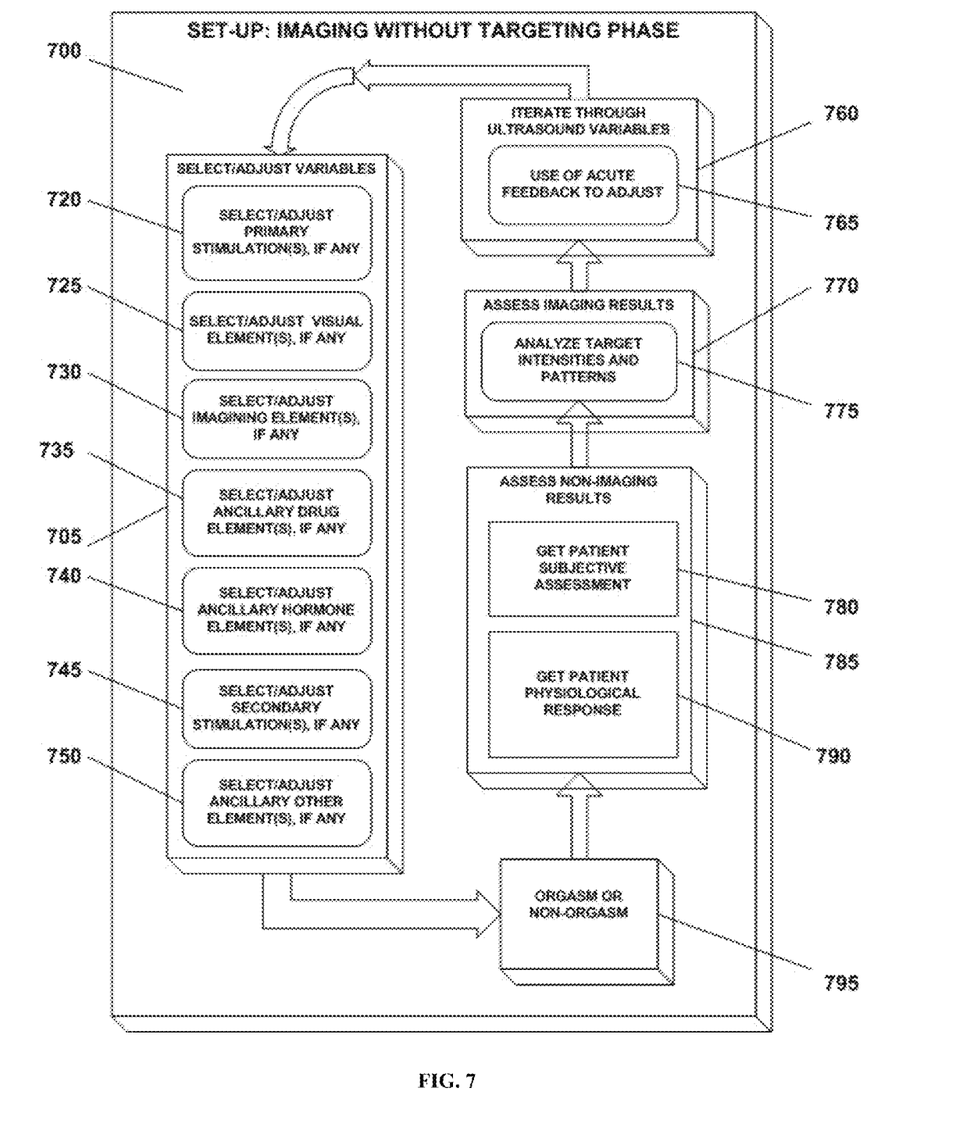
FIG. 7 Set-Up Imaging Phase.
Figure 8:
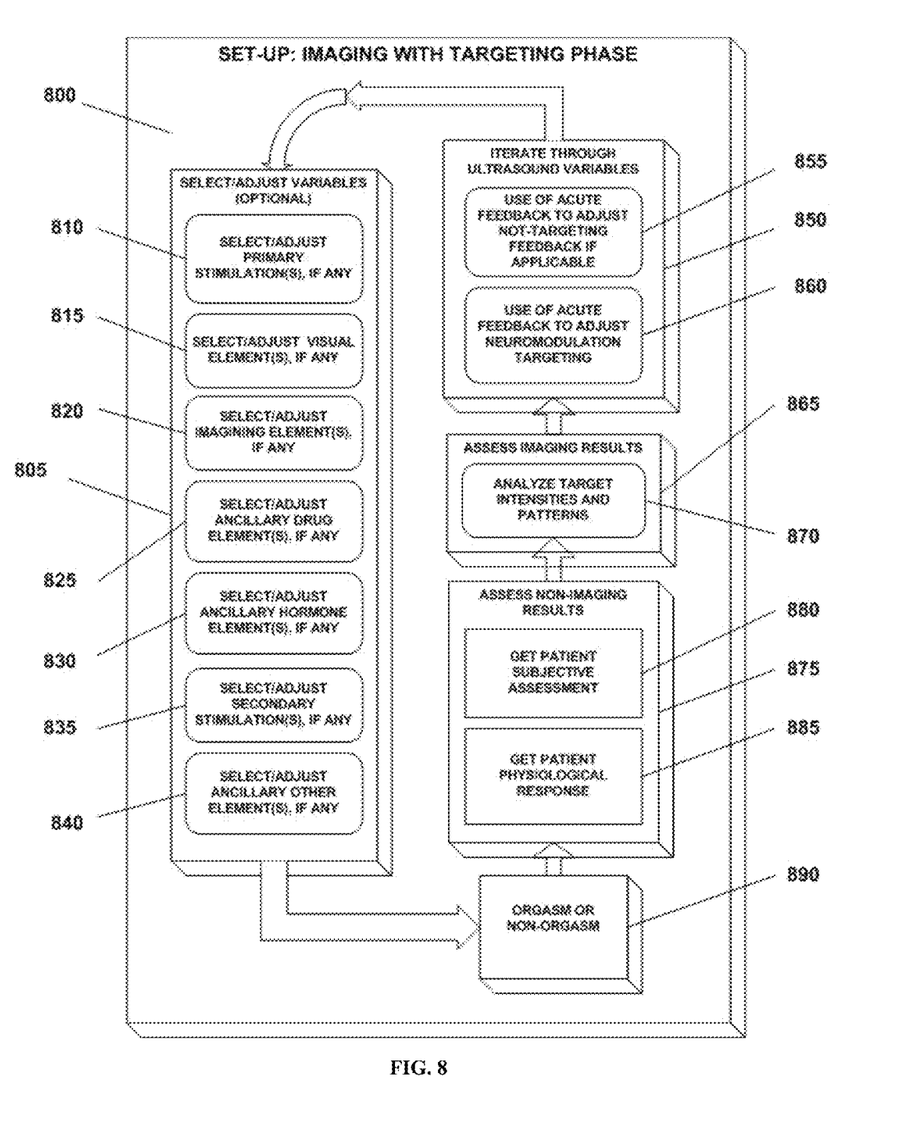
FIG. 8 Set-Up Imaging & Targeting Phase.

FIGS. 6, 7, and 8 show the various set-up phases, one or a plurality of which may be applied. In these phases and the utilization of the Orgasmatron, Primary Stimulation includes a selection of one or a plurality of external or internal genital stimulation using insertion, pressure, rubbing, vibration, other mechanical, electrical, thermal, ultrasound or other application of energy for tactile, pain, or other stimulation. Stimulation of any of the pelvic organs (e.g., clitoris, vagina, cervix, uterus, anus, rectum, prostate, and penis) can result in any orgasm. Visual Stimulation includes presentation of sexual partner, images of the sexual partner, self, couple together, pornography, sadomasochism, or any other excitatory material. This may be augmented by or substituted for by audio stimulation. Imagining refers to fantasizing by the subject. Ancillary Drug Elements include drugs for erectile dysfunction, mood alteration, or other applicable agents. For example drugs like bupropion that facilitate dopamine presence facilitate orgasms in both men and women. Ancillary Hormone Elements include sex-related hormones (e.g., estrogens and androgens) as well as thyroid or other applicable agents. Secondary Stimulations include non-genital stimulations such as nipples, skin areas in any application or other stimulations using an energy or energies as noted under Primary Stimulations above. It is noted that healthcare personnel can view the stimulations effective relative to a specific patient/subject in a non judgmental way. Note where longer-term changes are involved such as hormones or drugs, the process may take awhile so might want to go to imaging and/or real-time stimulation first. In any case situation may be important enough to patient for long term and/or increased benefit, may be worth the wait.

In the set-up phases the patient/subject physiologic results will include assessment of changes such as, but not limited to, blood pressure, pulse rate, respiratory rate, pupil diameter, pain threshold, and muscle contractions.

FIG. 6 illustrates the set-up in the non-imaging phase 600. Set of Select/Adjust Variables steps 605 has steps Select/Adjust Primary Stimulation(s), If Any 610, Select/Adjust Visual Element(s), If Any 615, Select/Adjust Imagining Element(s), If Any 620, Select/Adjust Ancillary Drug Element(s), If Any 625, Select/Adjust Ancillary Hormone Element(s), If Any 630, Select/Adjust Secondary Stimulation(s), If Any 635, and Select/Adjust Ancillary Other Element(s), If Any 640. Set Ultrasound neuromodulation is then applied (first time through with its default settings) followed by Orgasm or Non-Orgasm 680 which in turn is followed by set of steps in Assess Results 660 which consists of step Get Patient Physiological Response 670 and Get Patient Subjective Assessment 665. The final phase is Iterate Through Ultrasound Variables 650 with Use of Acute Feedback To Adjust 655 that iterates through the ultrasound variables (e.g., positions, intensity, frequency, phase/intensity relationships, pulse duration, firing pattern) which in turn is followed by Selection/Adjustment Variables 605. Note that as noted previously that Visual Element(s), If Any 615 may be replaced by or augmented with auditory-stimulation elements.

Note that while imaging is covered in the following sections, the invention can be used without imaging. FIG. 7 shows the Set-Up Imaging Without Targeting Phase 700, which can be done without or with the Set-Up Non-Imaging Phase 600 preceding it. Set-Up Imaging Phase 700 Set of Select/Adjust Variables steps 705 has steps Select/Adjust Primary Stimulation(s), If Any 720, Select/Adjust Visual Element(s), If Any 725, Select/Adjust Imagining Element(s), If Any 730, Select/Adjust Ancillary Drug Element(s), If Any 735, Select/Adjust Ancillary Hormone Element(s), If Any 740, Select/Adjust Secondary Stimulation(s), If Any 745, and Select/Adjust Ancillary Other Element(s), If Any 750. Ultrasound neuromodulation is then applied (first time through with its default settings) followed by Orgasm or Non-Orgasm 795 which in turn is followed by set of steps in Assess Non-Imaging Results 785 which consists of step Get Patient Physiological Response 790 and Get Patient Subjective Assessment 780. Assess Non-Imaging Results 785 is followed by Assess Imaging Results 770 which is Analyze Target Intensities and Patterns 775. The final phase is Iterate Through Ultrasound Variables 760 with Use of Acute Feedback To Adjust 765 that iterates through the ultrasound variables (e.g., positions, intensity, frequency, phase/intensity relationships, pulse duration, firing pattern) which in turn is followed by Selection/Adjustment Variables 705. Note that as noted previously that Visual Element(s), If Any 725 may be replaced by or augmented with auditory-stimulation elements. Note that imaging overall is optional, but may be particularly important in certain cases (e.g., for anorgasmic women or in anorgasmic or hypo-orgasmic post-prostate-surgical men). One can check for best target candidates even without orgasm based on the images resulting from the various forms of stimulations.

FIG. 8 shows the Set-Up Imaging With Targeting Phase 800 can be done alone or can follow either the Set-Up Imaging Without Targeting Phase 700 or Set-Up Non-Imaging Phase 600, or both. Set-Up Imaging With Targeting Phase 800 Set of Select/Adjust Variables (Optional) steps 805 has steps Select/Adjust Primary Stimulation(s), If Any 810, Select/Adjust Visual Element(s), If Any 815, Select/Adjust Imagining Element(s), If Any 820, Select/Adjust Ancillary Drug Element(s), If Any 825, Select/Adjust Ancillary Hormone Element(s), If Any 830, Select/Adjust Secondary Stimulation(s), If Any 835, and Select/Adjust Ancillary Other Element(s), If Any 840. Ultrasound neuromodulation is then applied (first time through with its default settings) followed by Orgasm or Non-Orgasm 890 which in turn is followed by set of steps in Assess Non-Imaging Results 875 which consists of step Get Patient Physiological Response 885 and Get Patient Subjective Assessment 880. Assess Non-Imaging Results 885 is followed by Assess Imaging Results 865 which is Analyze Target Intensities and Patterns 870 is performed. The final phase is Iterate Through Ultrasound Variables 850 with application of both Use of Acute Feedback to Adjust Neuromodulation 860 and Use of Acute Feedback to Adjust with Non-Targeting Feedback, If Applicable 855. These iterate through the ultrasound variables (e.g., positions, intensity, frequency, phase/intensity relationships, pulse duration, firing pattern). Iterate through Ultrasound Variables 850 is then in turn followed by Selection/Adjustment Variables 805, which is optional. Note that as noted previously that Visual Element(s), If Any 815 may be replaced by or augmented with auditory-stimulation elements. Note again that imaging overall is optional, but may be particularly important in certain cases (e.g., for anorgasmic women or in anorgasmic or hypo-orgasmic post-prostate-surgical men). Again, one can check for best target candidates even without orgasm.

Figure 9:
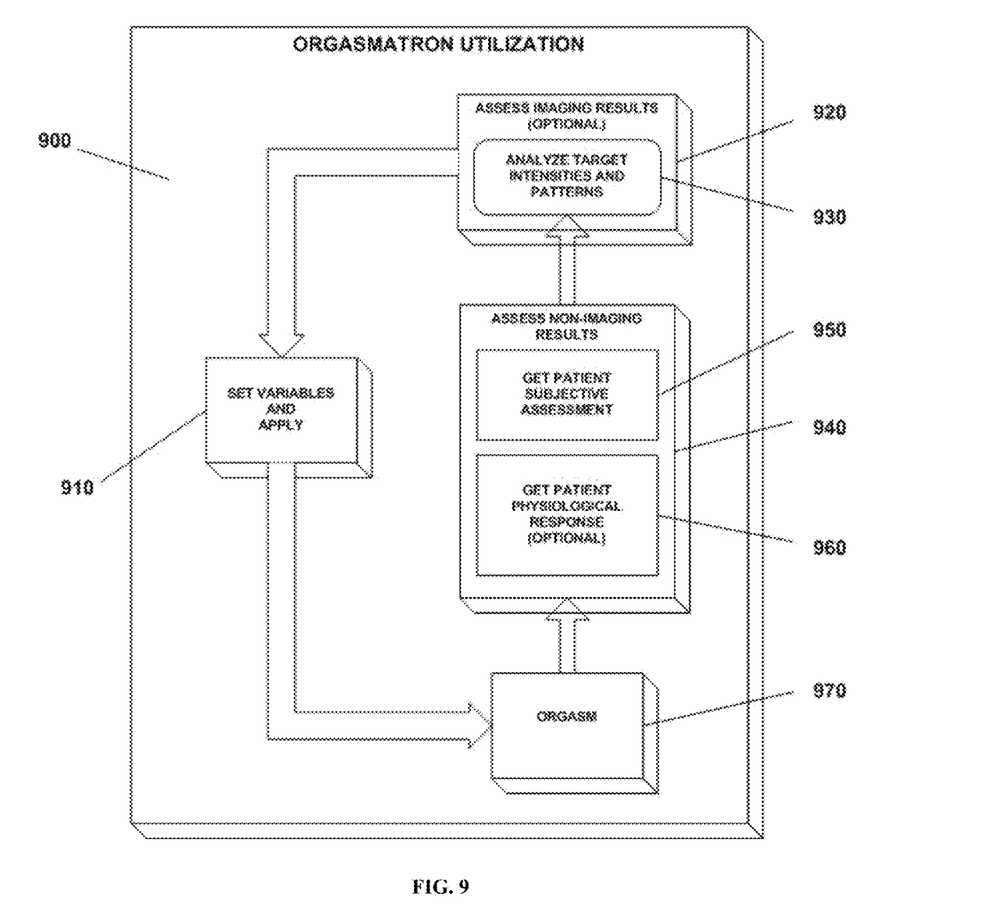
FIG. 9 Orgasmatron Utilization.

FIG. 9 illustrates Orgasmatron Utilization 900. Based on the previous set-up phases covered in FIGS. 6-8, Set Variables and Apply 910 is followed by Orgasm 970 which is followed by in turn followed by Assessment of Non-Imaging Results 940 which includes optional Get Patient Physiological Response 960 and Get Patient Subjective Assessment 950. Get Patient Subjective Assessment 950 could be optional, but is for practical purposes inherent. Assess Non-Imaging Results 940 is followed Assess Imaging Results (Optional) 920 which includes Analyzing Target Intensities and Patterns 930. This can includes Set Variables and Apply 910 in future sessions, which may be based on the application of one or a plurality of the set-up phases covered above in FIGS. 6 through 8. Note that previous studies by Komisaruk et al. have included assessment of imaging of couples in an open-frame scanner. Ultrasound stimulation uses smaller and less expensive devices than other means of deep-brain neuromodulation such as Transcranial Magnetic Stimulation. The current invention is sufficiently portable for home or other non-healthcare-setting use that is key to broad, practical use.

In another embodiment, all or part of the neuromodulation is provided by Radio-Frequency (RF) therapy, Transcranial Magnetic Stimulation (TMS), transcranial Direct Current Stimulation (tDCS), application of optogenetics, cryotherapy, stereotactic radiosurgery, and/or Deep Brain Stimulation (DBS) using implanted electrodes.

All of the embodiments above, except those explicitly restricted in configuration to hit a single target, are capable of and usually would be used for targeting multiple targets either simultaneously or sequentially. Hitting multiple targets in a neural circuit in a treatment session is an important component of fostering a durable effect through Long-Term Potentiation (LTP) and/or Long-Term Depression (LTD). In addition, this approach can decrease the number of treatment sessions required for a demonstrated effect and to sustain a long-term effect. Follow-up tune-up sessions at one or more later times may be required. Note that this neuromodulation-mediated Orgasmatron can be applied acutely for immediate orgasm or chronically, through multiple sessions, chronically, to facilitate future organism with or without acute neuromodulation.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

What is claimed is:

1. A method of neuromodulating one or a plurality of deep-brain targets using ultrasound stimulation, the method comprising:
   aiming one or a plurality of ultrasound transducers at one or a plurality of deep-brain targets selected from the group consisting of Temporal Lobe, Nucleus Accumbens, Hypothalamus, Paraventricular Nucleus, and Cerebellum;
   using a set-up phase imaging with targeting to determine settings of various selected neuromodulation variables;
   applying one or more non-ultrasound stimulations by selecting and adjusting each in the order of primary stimulations, visual elements, imagining elements, ancillary drug elements, ancillary hormone elements, ancillary secondary stimulations, and ancillary other elements;
   applying power to each of the ultrasound transducers via a control circuit thereby modulating the activities of the deep brain target regions according to the settings determined during set-up;
   whereby an orgasm is elicited in response to the ultrasound neuromodulation and non-ultrasound stimulation.

2. The method of claim 1, wherein one or a plurality of primary stimulations is applied to a region selected from the group consisting of external pelvic organ stimulation, internal pelvic organ stimulation, and other body area using one or a plurality of stimulation mechanisms selected from the group consisting of insertion, pressure, rubbing, vibration, other mechanical, electrical, thermal, ultrasound, tactile, pain, and other stimulation.

3. The method of claim 2, wherein one or a plurality of pelvic organs is selected from the group consisting of clitoris, vagina, cervix, uterus, anus, rectum, prostate, and penis.

4. The method of claim 1, wherein one or a plurality of secondary stimulations is applied to a region selected from the group consisting of external pelvic organ stimulation, internal pelvic organ stimulation, and other body area using one or a plurality of stimulation mechanisms selected from the group consisting of insertion, pressure, rubbing, vibration, other mechanical, electrical, thermal, ultrasound, tactile, pain, and other stimulation.

5. The method of claim 4, wherein one or a plurality of pelvic organs is selected from the group consisting of clitoris, vagina, cervix, uterus, anus, rectum, prostate, and penis.

6. The method of claim 1, wherein one or a plurality of visual elements is selected from the group consisting of sexual partner, image of sexual partner, image of self, image of couple together, pornography, sadomasochism, and other material excitatory to viewer.

7. The method of claim 1, wherein visual element is augmented by or substituted for by auditory element.

8. The method of claim 1, wherein the orgasm is used to treat the condition selected from the group consisting of anorgasmia, hypo-orgasmia, facilitation of having orgasms, and hedonia.

9. The method of claim 1, wherein ultrasound therapy is combined with or replaced by one or more therapies selected from the group consisting of medications, Radio-Frequency (RF) therapy, application of optogenetics, Transcranial Magnetic Stimulation (TMS), transcranial Direct Current Stimulation (tDCS), cryotherapy, stereotactic radiosurgery, and Deep Brain Stimulation (DBS) using implanted electrodes.

10. The method of claim 1 where set-up with imaging with targeting is preceded by one or a plurality of phases selected from the group consisting of set-up using a non-imaging and set-up using imaging without targeting.

11. A method of neuromodulating one or a plurality of deep-brain targets using ultrasound stimulation, the method comprising:

aiming one or a plurality of ultrasound transducers at one or a plurality of deep-brain targets selected from the group consisting of Left Orbito-Frontal Cortex, Dorsal Anterior Cingulate Gyms, Hippocampus and Caudate Nucleus;

using a set-up phase imaging with targeting to determine settings of various selected neuromodulation variables applying one or more non-ultrasound stimulations by selecting and adjusting each in the order of primary stimulations, visual elements, imagining elements, ancillary drug elements, ancillary hormone elements, ancillary secondary stimulations, and ancillary other elements;

applying power to each of the ultrasound transducers via a control circuit thereby modulating the activities of the deep brain target regions according to the settings determined during set-up;

whereby an orgasm is elicited in response to the ultrasound neuromodulation and non-ultrasound stimulation.

12. The method of claim 11, wherein one or a plurality of primary stimulations is applied to a region selected from the group consisting of external pelvic organ stimulation, internal pelvic organ stimulation, and other body area using one or a plurality of stimulation mechanisms selected from the group consisting of insertion, pressure, rubbing, vibration, other mechanical, electrical, thermal, ultrasound, tactile, pain, and other stimulation.

13. The method of claim 12, wherein one or a plurality of pelvic organs is selected from the group consisting of clitoris, vagina, cervix, uterus, anus, rectum, prostate, and penis.

14. The method of claim 11, wherein one or a plurality of secondary stimulations is applied to a region selected from the group consisting of external pelvic organ stimulation, internal pelvic organ stimulation, and other body area using one or a plurality of stimulation mechanisms selected from the group consisting of insertion, pressure, rubbing, vibration, other mechanical, electrical, thermal, ultrasound, tactile, pain, and other stimulation.

15. The method of claim 14, wherein one or a plurality of pelvic organs is selected from the group consisting of clitoris, vagina, cervix, uterus, anus, rectum, prostate, and penis.

16. The method of claim 11, wherein one of a plurality of visual elements is selected from the group consisting of sexual partner, image of sexual partner, image of self, image of couple together, pornography, sadomasochism, and other material excitatory to viewer.

17. The method of claim 11, wherein visual element is augmented by or substituted for by auditory element.

18. The method of claim 11, wherein the orgasm is used to treat the condition selected from the group consisting of anorgasmia, hypo-orgasmia, facilitation of having orgasms, and hedonia.

19. The method of claim 11, wherein ultrasound therapy is combined with or replaced by one or more therapies selected from the group consisting of medications, Radio-Frequency (RF) therapy, application of optogenetics, Transcranial Magnetic Stimulation (TMS), transcranial Direct Current Stimulation (tDCS), cryotherapy, stereotactic radiosurgery, and Deep Brain Stimulation (DBS) using implanted electrodes.

20. The method of claim 11, where set-up with imaging with targeting is preceded by one or a plurality of phases selected from the group consisting of set-up using a non-imaging and set-up using imaging without targeting.

* * * * *